United States Patent [19]

Sato et al.

[11] E Patent Number: Re. 32,162

[45] Reissued Date of Patent: May 27, 1986

[54] PRESSURE SENSITIVE RECORD MATERIAL EMPLOYING DIARYL ALKANE SOLVENTS

[75] Inventors: Atsushi Sato, Tokyo; Yoshiaki Aida; Isoo Shimizu, both of Yokohama, all of Japan

[73] Assignee: Nippon Petrochemicals Co., Ltd., Tokyo, Japan

[21] Appl. No.: 70,711

[22] Filed: Aug. 29, 1979

Related U.S. Patent Documents

Reissue of:

[64] Patent No.: 3,936,566
Issued: Feb. 3, 1976
Appl. No.: 407,986
Filed: Oct. 19, 1973

U.S. Applications:

[62] Division of Ser. No. 229,195, Feb. 24, 1972, abandoned.

[30] Foreign Application Priority Data

Mar. 2, 1971 [JP] Japan ..... 46-10542
Mar. 15, 1971 [JP] Japan ..... 46-13965

[51] Int. Cl.[4] ..... B41M 5/16; B41M 5/22

[52] U.S. Cl. ..... 346/213; 282/27.5; 346/218; 427/150; 428/323; 428/402.2; 428/537.5; 428/913; 428/914

[58] Field of Search ..... 428/323, 315.5, 402.2, 428/537.5, 913, 914; 346/207, 213, 218; 8/513; 282/27.5; 252/316; 570/199; 549/225; 427/150

[56] References Cited

U.S. PATENT DOCUMENTS

| | | | |
|---|---|---|---|
| 3,009,760 | 11/1961 | Lenz | 8/513 |
| 3,016,308 | 1/1962 | Macaulay | 282/27.5 |
| 3,069,478 | 12/1962 | McLaughlin | 570/199 |
| 3,625,736 | 12/1971 | Matsukawa et al. | 282/27.5 |
| 3,627,581 | 12/1971 | Phillips | 252/316 |
| 3,649,649 | 3/1972 | Orita et al. | 428/402.2 |
| 3,669,728 | 6/1972 | Seiner | 428/315.5 |
| 3,738,857 | 6/1973 | Brockett et al. | 346/207 |
| 3,836,383 | 9/1974 | Kiritani et al. | 252/316 |
| 3,936,566 | 2/1976 | Sato et al. | 428/323 |

FOREIGN PATENT DOCUMENTS

| | | |
|---|---|---|
| 540383 | 4/1957 | Canada . |
| 585073 | 1/1947 | United Kingdom . |
| 915342 | 1/1963 | United Kingdom . |

OTHER PUBLICATIONS

Malan, J. Appl. Chem. Biotechnol. 1972, 22, pp. 959-965.

Best, R. "Physical Properties of Diarylalkanes," *J. Chem. Eng. Data*, vol. 8, No. 2, pp. 267-270 Apr. 1963.

Kirk-Othmer Encyclopedia of Chemical Technology, second completely revised edition, vol. 6, pp, 524-525 (1965).

International Encyclopedia of Chemical Science, published by Van Nostrand Co, Inc. p. 476 (1964).

Fox, Labes and Weissberger, ed., *Physics and Chemistry of the Organic Solid State, vol. 1, Interscience Publishers, pp. 73-74 (Dec. 1963).*

Fox, Labes and Weissberger, ed., *Physics and Chemistry of the Organic Solid State*, vol. 2, Interscience Publishers, pp. 725-728 (Apr. 1965).

Bielstein, Hand Buch Organischen Chemie, E III 5 pp. 1915 and 1923 (1964) and E IV 5 pp. 1926-1927 (1979).

Chemical Abstracts, vol. 69, p. 244, Abstract No. 2592t (1968).

Chemical Abstracts, vol. 73, Abstract No. 57100U (1970).

*Primary Examiner*—Thomas J. Herbert
*Attorney, Agent, or Firm*—Fisher, Christen & Sabol

[57] ABSTRACT

A solvent for the pressure sensitive record material which consists of a normally liquid compound having 13 to 18 Carbon atoms and being represented by the following general formula:

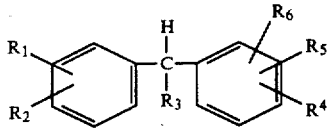

in which each of $R_1$ to $R_5$ is hydrogen, methyl group or etyl group $R_6$ is hydrogen, methyl, ethyl, iso-propyl, n-propyl, tert-buthyl or sec-buthyl group; and the preparation method of the above solvent from styrene and $C_7$-$C_{10}$ aromatic hydrocarbons using sulfuric acid as the catalyst.

16 Claims, No Drawings

PRESSURE SENSITIVE RECORD MATERIAL EMPLOYING DIARYL ALKANE SOLVENTS

Matter enclosed in heavy brackets [ ] appears in the original patent but forms no part of this reissue specification; matter printed in italics indicates the additions made by reissue.

This is a division of application Ser. No. 229,195, filed Feb. 24, 1972, now abandoned.

This invention relates to a solvent or a vehicle for a pressure sensitive record material and the preparation method therefor.

Further, the invention relates to the solvent for the pressure sensitive record material which has excellent properties such as non-toxicity for the health, good solubility for dyeprecursor and good durability after recorded.

In the prior art, several pressure sensitive record materials are well known, in which, for example, a sheet of paper is applied with microcapsules containing a solution of dyeprecursor, and another sheet of paper is applied with clay or polymeric material which produces a colour by reacting with said colourless dyestuff, both of said treated surfaces are then put together with each other, thereafter the set of paper is applied with a local pressure by hand writing or type writing to obtain a colored impression as desired.

The recording mechanism in this type of pressure sensitive record material is such that the microcapsules are ruptured by the pressure of hand writing or the impact of type writing to release the colouring solution containing the colouring agent as an electron donor dyestuff in the microcapsules, then it contacts with the clay or polymeric material as an electron acceptor on the opposed surface of said another paper to produce a colour.

In another form of a known record material, the microcapsule layer is applied on one side surface of a sheet of paper as an inner layer and the clay or polymeric material layer is then applied thereon as an outer layer. In like manner as the foregoing one, when it is used, the microcapsules on this record material are ruptured by the pressure of hand writing or type writing, then the colouring solution containing a dyestuff in the microcapsules is released, and it contacts with the clay or polymeric material on the outer layer to produce a colour.

The solution of the colouring agent as used for these record material is that of a colourless dyestuff of an electron donor in one or more of hydrophobic solvents. And said hydrophobic solvents are required to have the following properties.

That is, the solvents must have no acute toxicity, no chronic toxicity, no disagreeable odor, no colour or a slight colour, non-volatility, good solubility for the dyestuff and good stability when the dyestuff is dissolved. It is further required that, in the formation of the microcapsules, a stable and very fine dispersion of the colouring agent solution can be produced; the membrane of the capsule can be formed on the particle of said dispersion, the storage stability of the microcapsule thus formed is good; said membrane of the microcapsule is of uniform and of desired thickness; the solvent does not inhibit the colour forming reaction between the dyestuff and the clay or the polymeric material with a high reaction rate; when paper coated with a polymeric material is used, the solvent dissolves said polymeric material to cause a close contact with the dyestuff; the copied impression is clear without runs; and that the record can be kept as it is without any change for a long period of time.

In the conventional art, the solvent as generally employed for the preparation of the microcapsules of these pressure sensitive record material, has been polychlorinated biphenyl. It is true that the polychlorinated biphenyl has several excellent properties as the solvent of this kind, however, it has a serious disadvantage that it is toxic for the health because, when it is absorbed in human body, it can neither be decomposed nor be purged and gives a chronic toxicity. Accordingly, it is earnestly desired to find a solvent of the dyestuff for the microcapsules which has excellent properties and no such toxicity.

In order to meet these requirements, partially nuclear hydrogenated terphenyl compounds

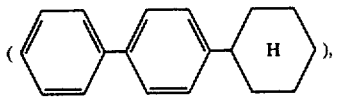

alkyl naphthalene compounds and alkyl biphenyl compounds have been used as the solvents therefor, however, they are not so good in the solubility and the color forming rate. So that they are not satisfactory as the solvents for preparing the pressure sensitive record material.

Accordingly, the object of the present invention is to provide novel solvents of the dyestuff for the microcapsule of the pressure sensitive record material which have excellent properties and have no toxicity for the health as being caused by said chlorinated biphenyl, and further to propose the method preparing the same.

That is, the solvents of the present invention for the pressure sensitive record material are normally liquid compounds each having 13 to 18 carbon atoms, which are represented by the following general formula:

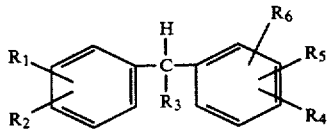

(I)

in which each of $R_1$ to $R_5$ is hydrogen, methyl group or ethyl group, $R_6$ is hydrogen, methyl, ethyl, iso-propyl, n-propyl, tertbuthyl or sec-buthyl group.

The compounds being represented by the above general formula (I) are stable, high boiling and non-volatile ones, and when the number of carbon atoms of each compound exceeds 18, the solubility for the dyestuff is decreased and it can not be advantageously used as the solvent for this purpose.

In the compounds as defined by the above general formula (I), when each of the group $R_3$ is a hydrogen, they can be prepared by reacting benzyl chloride or its derivative with toluene, xylene or ethylbenzene in the presence of Friedel-Crafts catalyst, or by reacting formaldehyde with toluene, xylene or ethylbenzene. The following compounds in this group are preferably used as the solvents.

(II)

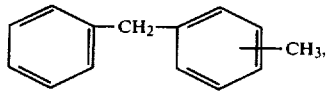

(III)

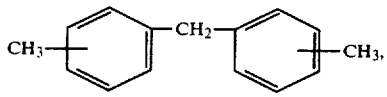

(IV)

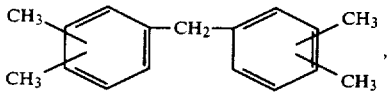

(V)

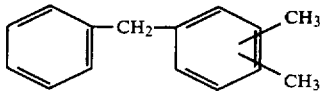

(VI)

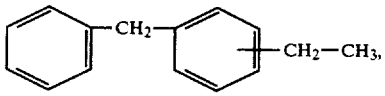

and (VII)

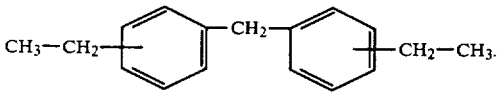

When $R_3$ is methyl group, they can be prepared by reacting, for example, styrene or vinyl toluene with $C_7$–$C_{10}$ aromatic hydrocarbons. The following compounds of this group are preferably used, (VIII)

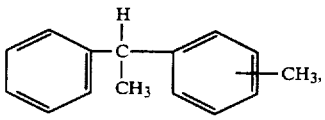

(IX)

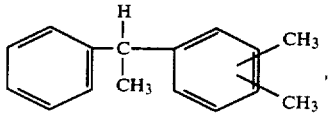

(X)

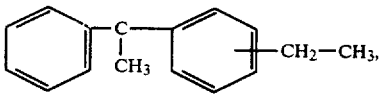

(XI)

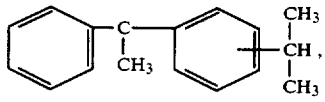

and (XII)

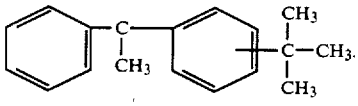

The above compounds, (VIII), (IX), (X), (XI), and (XII), can be produced by the reaction between styrene and $C_7$–$C_{10}$ aromatic hydrocarbons, however, a highly pure product with good yield can not be expected through the simple known reaction between them. The present invention employing toluene and $C_8$-aromatics will be mainly described hereinafter. It can, however, be carried out in the same way either by utilizing $C_9$- or $C_{10}$-aromatics.

For example, when toluene or $C_8$-aromatics is mixed with styrene and the reaction is carried out by heating or in the presence of a radical catalyst, only styrene polymer can be obtained. On the other hand, as disclosed in Comparative Examples described hereafter, if the Friedel-Crafts catalysts such as aluminium chloride, hydrogen fluoride and boron trifluoride are used, much of resinous product is formed and the object product can not be obtained effectively.

As the result of the extensive investigations by the inventors of the present invention, a novel method for preparing the above-mentioned compound (VIII), (IX) or (X) by the reaction of toluene or $C_8$-aromatics with styrene has been found.

When this method is carried out by a batch process to produce the compound as shown by the structural formula (VIII), (IX) or (X), it is characterized in that sulfuric acid is used as the catalyst, the concentration of which is kept at 75 to 90% in the reaction system, and the reaction is conducted at a temperature of lower than 30° C. with agitation. Further, another characteristic feature in the batch process is that concentrated sulfuric acid of 90% or more is added into the reaction mixture after the above reaction in order to minimize the unreacted styrene in the reaction system.

Said compounds as indicated by the structural formulae (VIII), (IX) or (X) can be commercially produced preferably by a continuous process.

In the continuous process of the reaction between toluene or $C_8$-aromatics and styrene, it is characterized in that sulfuric acid is also used as the catalyst in the continuous flow of the reaction mixture, the concentration of the catalyst is kept at 80 to 96% in the reaction system, the content of styrene in the reaction system is kept at less than 5% by weight against the sum of the reactants.

The $C_8$-aromatics as referred to in this specification may be o-xylene, m-xylene, p-xylene, ethylbenzene or a mixture of them.

The xylene fraction of aromatic hydrocarbons having 8 carbon atoms can be used which is obtained as the by-product in the production of lower olefins through the thermal cracking or steam cracking of petroleum, or the xylene fraction from the production of aromatic compounds by the catalytic cracking or the reforming of petroleum can be also employed. In the method of the present invention, m-xylene is most preferably used.

When a mixture of $C_8$-aromatics is used as the raw material, the following method can be applied. That is, the $C_8$-aromatic fraction which is obtained by the cracking of crude oil, naphtha cracking or dealkylation process is used as it is, or if necessary, it is added with ethylbenzene to be used. Thus the fraction containing more than 30% by weight of ethylbenzene in addition to xylenes is treated under the condition that the ethylbenzene is dehydrogenated to produce styrene, thereafter the reaction product is used as it stands without separating the produced styrene for the above-mentioned reaction process to form the compound as defined by the structural formula (VIII), (IX) or (X).

In the following, the method of the present invention for preparing the compounds as defined by the above formulae (VIII), (IX) or (X) will be further explained in detail.

In the continuous process of a commercial scale, the concentration of sulfuric acid catalyst is to be kept within the range from 80 to 96% in the reaction system. When the concentration if the catalyst exceeds 96%, especially 98%, sulfonation reaction is caused to occur which results in the lowering of the yield of product, and further the separation and recovery of the product become difficult as the reaction mixture is emulsified. On the other hand, if the concentration of the sulfuric acid catalyst is less than 80%, the reaction can not be made to proceed effectively and the corrosion of apparatus is apt to occur. The sulfuric acid is generally recycled, however, when it is added into the reaction system, if the sulfuric acid is diluted by the water contained in the recycled xylene or toluene, sulfuric acid of about 98% may be used.

The amount of sulfuric acid to be used in the method of the present invention is from 10 to 200% by weight, preferably from 50 to 150% by weight against the amount of styrene as used.

The reaction vessel for this process may be a reaction tank with an agitator or a shell-and-tube reactor to cause a sufficient turbulent flow of the reaction mixture, and it must be provided with effective coolers.

During the reaction of this invention, the concentration of styrene in the reaction mixture is to be kept at not more than 5% by weight. If more than 5% of styrene is contained in the reaction system, the side reactions such as polymerization and sulfonation is increased, and in addition to that, the purity of sulfuric acid being used as the catalyst is decreased so that the recovering and re-use of the sulfuric acid can not be attained. In the method of the present invention, it is preferable that the concentration of styrene in the reaction system may be kept within the range from 0.5 to 3% by weight.

On account of the above reason, an extremely excess amount of the other reaction material, i.e. xylene or toluene, may be used, or an inactive solvent may be used in the process of the present invention. As for said inactive solvent, aliphatic hydrocarbons and aromatic hydrocarbons can be used, however, the former aliphatic hydrocarbons are preferable because most of the aromatic hydrocarbons are not completely inactive.

In the preferable reaction condition of the method of the present invention, one reaction of $C_8$-aromatics or toluene and the catalyst of sulfuric acid of a certain concentration are introduced into a reactor, then the inactive solvent is added or not added, and a certain amount of the other reactant of styrene is fed thereto, where the concentration of the styrene is controlled by adding with further recycle or make-up $C_8$-aromatics or toluene or inactive solvents continuously. This step is desirable for the controls of the concentration of the reaction mixture which is further explained in the following.

It is necessary for the process of the invention to keep the reaction temprature at lower than 30° C. in the condition of stirring or turbulent flow. If the reaction is carried out at a temprature of higher than 30° C., the rate of side reaction such as sulfonation is rapidly increased, and the overall reaction rate is raised to generate intensely a large amount of heat of reaction, and the control of the temperature become difficult, which further causes the side reaction, and therefore the objective compound can not be produced.

In the method of the present invention, the reaction is preferably carried out at a temperature in the range of 5° to 20° C., accordingly the reactor must be provided with an insise or outside cooler.

In the reaction of the present invention, it is further necessary that the concentration of the produced $C_8$-aromatics derivative or toluene derivative [structural formula (VIII), (IX) or (X)] in the reaction mixture is to be kept at less than 50% by weight.

As disclosed in the above, the reaction of the present invention is carried out by allowing styrene of less than a certain concentration to react with excess $C_8$-aromatics or toluene. In this case, if the concentration of the product, $C_8$-aromatics derivative of toluene derivative [structural formula (VIII), (IX) or (X)] exceeds 50% by weight, a side reaction is caused to occur to form heavier materials, therefore an effective reaction can not be attained. With regard to the pressure of the reaction, there is no restriction, however, the reaction may be preferably carried out at the normal pressure or at the self-pressure of the reaction.

With regard to the reaction time in the method of the present invention, there is also no restriction. While, the rate of reaction is relatively high, therefore a long period retention of the reaction gives no advantage, and causes only the increase of the side reaction. The average retention time may be preferably in the range of 5 minutes to 1 hour.

After the reaction of this invention, the reaction mixture is transferred from the reactor to a sulfuric acid settler, and is allowed to standstill. The sulfuric acid of the bottom layer in the settler is recovered and recycled to the reactor. Most of the reaction product, unreacted materials and by-products are contained in the upper hydrocarbon layer. The separated hydrocarbon layer is then transferred to a soda-washing tank, and the residual sulfuric acid is neutralized by an aqueous alkaline solution. In this step, if the product of sulfonation as a side reaction is contained in a large amount, emulsification is caused and the separation by settling becomes difficult. And further, if the objective reaction product exceeds 50% by weight in the layer, the settling takes a long time and the separation becomes also difficult. The upper layer in the alkali washing step is then transferred to a water washing tank and is washed sufficiently with water. Thereafter, the washed reaction mixture is treated by a conventional distillation process to separate the desired product. The temperature at the bottom of the distillation column is preferably lower than 210° C., and if said temperature is too high, the colour and odor of the product is influenced for bad, and it is not desirable for the purity of the product. By the way, the separated unreacted $C_8$-aromatics or toluene is recycled to the reactor.

In the following, the batchwise process of the present invention will be explained.

In the batchwise process according to the method of the present invention, the reaction can be carried out substantially in like manner as that in the foregoing continuous process. However, if sulfuric acid of a high concentration is used from the initial stage of the reaction, the side reaction such as sulfonation is liable to occur, accordingly sulfuric acid of a lower concentration (about 75 to 90%) may be preferably employed when the reaction is carried out in one step. And further, the concentration of styrene in the reaction system is preferably maintained at less than 5% by weight in order to minimize the side reaction. However, it is presumed that the residual unreacted styrene causes side reaction in the separation step to form impurities, therefore the reaction may be carried out in two steps, that is, after the above first reaction, sulfuric acid of a higher concentration of more than 90% is added into the reaction mixture to cause the residual styrene to react with $C_8$-aromatics or toluene completely. Cumene, n-propylbenzene, sec-butylbenzene, tert-butylbenzene, a mixture thereof, or a mixture of the said hydrocarbon and other aromatic hydrocarbons such as $C_9$- or $C_{10}$-fractions obtained fom naphtha cracking may be exemplified as a typical $C_9$- or $C_{10}$-aromatic hydrocarbons. These aromatic hydrocarbons can be processed in the same manner as the above in order to attain the intended product of the present invention.

The compounds as defined by the aforementioned general formula (I) which are obtained by any other process except the above processes, can be used as the solvent of the present invention. The compounds of the general formula (I) can be used solely or in a mixture as the solvent with excellent properties. Namely, it is an excellent solvent for the pressure sensitive record material, because it has no toxicity like chlorinated biphenyl, has no disagreeable odor and has several required properties for the use. In addition to that, the solvent of the present invention is high boiling and non-volatile so that the microcapsule being prepared by using this solvent can be stored for a long period of time as it is. When the solvent is used, the dyestuff in the amount of 1 to 7%, preferably 3 to 5%, is dissolved therein, and of course, the solvents of the present invention have sufficient solubility for the materials to be dissolved.

As for the dyestuffs being used for the pressure sensitive record material, diarylphthalide, leucauramine, acyluramine, $\alpha,\beta$-unsaturated arylketone, basic monoazo dye, Rhodamine B lactam such as N-(p-nitrophenyl) Rhodamine B lactam, polyaryl carbinol and 8'-methoxy benzoindolino spiropyran (represented as 8'-methoxy BIPS) may be exemplified.

The above dyestuffs are electron donative ones, while the clay or polymeric materials to be contacted with the dyestuffs are of an electron acceptor, and as for said polymeric materials, phenol-aldehyde polymer, phenol-acetylene polymer, maleic acid-rosin polymer, partially or completely hydrolyzed styrene-maleic anhydride copolymer, partially or completely hydrolyzed ethylenemaleic anhydride copolymer, carboxy polyethylene and partially or completely hydrolyzed vinylmethyl ether-maleic anhydride copolymer may be exemplified.

As the method to form the microcapsule from the solution prepared by dissolving said dyestuff into the solvent of the present invention, there is a coacervation method in which the fine particles of the solution dispersed in water is coated by protective colloidal material such as gelatine or gum arabi. (cf. U.S. Pat. Nos. 2,712,507, 2,730,547; and 2,800,438). Another method therefor is the interfacial polymerization method in which monomer, intermediate or partially condensed product is used, and polymerization initiator, accelerator or catalyst is added thereto to cause the polymerization on the surface of the fine particles of the dye solution, thereby the microcapsule containing the colouring agent solution is prepared. The solvents of the present invention can be used for both of the above methods. In the practical process for preparing the microcapsule, an auxiliary solvent is used in order to control the viscosity and volatility of the dye solution, the particle size of the fine dispersion, the solubility to the polymeric material on the surface to be recorded and the rate of colour formation. However, the solvents of the present invention can be used effectovely without such auxiliary solvent, while, an inactive solvent which does not inhibit the characteristics of the solvent of the present invention, can be used as the auxiliary solvent. When the auxiliary solvent is used, the amount thereof may be less than two weight parts against one weight part of the solvent of the present invention.

In order that those skilled in the art may better understand the present invention and the manner in which it may be practised, the following specific examples are given.

EXAMPLE 1

Continuous preparation method for the compound of the structural formulae (IX) and (X)

A reactor was fed with the following materials:

| | |
|---|---|
| $C_8$-aromatics (mixed: o-xylene: 32.8% m-xylene: 37.6%, p-xylene: 19.6%, and ethylbenzene: 10%) | 10.0 kl/hr |
| Styrene | 0.3 kl/hr |
| Recycle $C_8$-aromatics | 1.5 kl/hr |
| Sulfuric acid | 0.5 kl/hr |

Said reactor was a shell-and-tube type and cooled by propylene coolant to remove the heat of reaction. The reaction mixture was recycled by a pump through the tubes causing turbulent flow to effect stirring. The average retention time of the reaction mixture was 30 minutes and the reaction temperature was controlled at about 10° C.

The reaction mixture from the reactor was transferred to a sulfuric acid settler to separate the sulfuric acid and hydrocarbons. The recovered sulfuric acid was recycled to the reactor and new make-up sulfuric acid was added as occasion demanded. The residual acid in the hydrocarbon layer was removed by the next scrubber, then the alkali content was removed by a water scrubber, thereafter most of the unreacted $C_8$-aromatics was removed by a flash drum, and then thus treated mixture was fed into a distillation system. By the distillation, the light fraction and heavy fraction were removed to obtain about 430 kg/hr of the product.

EXAMPLE 2

Using the following materials, the preparation of the solvent was carried out in like manner as Example 1.

| | |
|---|---|
| O—xylene | 0.35 kl/hr |
| Styrene | 0.3 kl/hr |
| Recycle xylene | 1.5 kl/hr |
| Sulfuric acid | 0.5 kl/hr |

As the result, about 450 kg/hr of the product was obtained, which had the following structural formula:

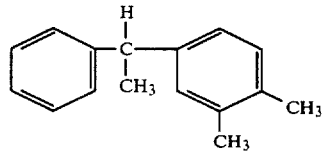

EXAMPLE 3

A $C_8$-aromatic fraction (ethylbenzene content: 45%) which was obtained from naphtha cracking was dehydrogenated under the following conditions:

| | |
|---|---|
| Reaction temperature | 550–650° C. |
| Reaction pressure | 0.2–1.0 Kg/cm$^2$ |
| LHSV | 0.2–1.0 vol/vol/hr |
| STM/EB | 2.0–3.0 wt. |
| Catalyst | $Fe_2O_3$, $K_2CO_3$, $Cr_2O_3$ |

To a 5 liter stainless steel reactor with a stirrer containing 1000 ml of the $C_8$-aromatics mixture which was not dehydrogenated and 200 grams of 90% sulfuric acid, was fed 500 ml of the above obtained styrene $C_8$-aromatics mixture containing 27.8 wt % of styrene, 13.5 wt % of p-xylene, 28.0 wt % of m-xylene and 6.8 wt % of o-xylene. The feeding of said mixture was carried out slowly during 20 minutes with agitation and cooling by using ice. The reaction temperature was kept at 15° C., and the stirring was continued for 1 hour, and after the reaction, the reaction mixtuer was settled and separated in like manner as the foregoing Example 1.

The product obtained was a mixture consisting of the compounds as defined by the following structural formula:

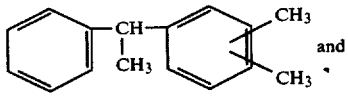

and

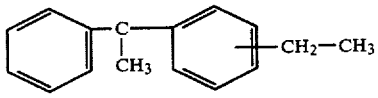

The purity of the colorless product was very high and the bromine value of the product was 0.01, and the yield against the styrene was 89% by mol.

EXAMPLE 4

Into a 5 liter stainless steel reactor with a stirrer was fed 2500 ml of m-xylene and 500 grams of 80% sulfuric acid, and the reactor was cooled externally by using ice. Said mixture is added slowly with 250 ml of styrene during 30 minutes with stirring. The reaction temperature was kept at 15°±5° C. and after the addition of the styrene, the agitation was further continued for 40 minutes. After that the agitation was stopped and the reaction mixture was stood still for 30 minutes. Then the sulfuric acid in the bottom layer was removed, and 1000 ml of 3% NaOH aqueous solution was added and stirred to nuetralize the residual sulfuric acid and a small amount of sulfonation product. The mixture was then settled again to remove the alkali layer, and after the removal of the alkali layer, 1500 ml of water was added and stired to wash. This water washing was repeated 4 times, and after the hydrocarbon layer was fed into a distillation column with ten plates to separate the reaction product. The temperature of the bottom was kept at about 200° C. Thereby, removing the initial distillation, 400 ml of the reaction product was recovered and it was analyzed by means of gas chromatography. It was understood by gas chromatography, MS and NMR that the reaction product was xylene derivatives containing mainly the following compound:

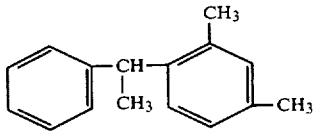

EXAMPLE 5

Into a 5 liter stainless steel reactor with a stirrer and an external cooler, 2500 ml of toluene and 500 grams of 82% sulfuric acid were introduced and the reactor was cooled. Then 250 ml of styrene was slowly added into the mixture during 30 minutes. The temperature of the reaction mixture was kept at 15°±5° C. After the addition of the styrene, the stirring was continued for 40 minutes, thereafter the reaction mixture was treated and the product was recovered in like manner as Example 1.

The reaction product obtained was the compound as indicated by the following structural formula, which is colourless, of no disagreeable odor, high purity and of good solubility. The yield of the product was 82% by mol against the styrene.

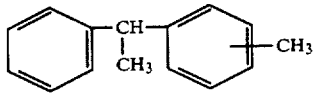

EXAMPLE 6

The following were processed in the same manner as in Example 1.

| | |
|---|---|
| Isopropylbenzene | 0.35 kl/hr |
| Styrene | 0.3 kl/hr |
| Recycle isopropylbenzene | 1.5 kl/hr |
| Sulfuric acid | 0.5 kl/hr |

As a result, a product was obtained in amount of about 410 Kg/hr and the product had the following structural formula;

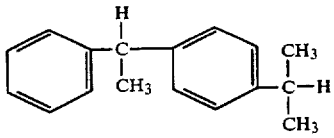

EXAMPLE 7

A $C_8$-aromatic fraction having the following composition which was obtained from naphtha cracking was treated in the same manner as in Example 1.

| | |
|---|---|
| $C_9$-aromatic fraction | 0.6 kl/hr |
| Styrene | 0.3 kl/hr |
| Recycle $C_9$-aromatic fraction | 2.0 kl/hr |
| Sulfuric acid | 0.5 kl/hr |

The composition of the fraction was as follows;

| | |
|---|---|
| n-Propylbenzene | 15 wt % |
| Isopropylbenzene | 4 wt % |
| o-Ethyltoluene | 17 wt % |

-continued

| | |
|---|---|
| m-Ethyltoluene | 24 wt % |
| p-Ethyltoluene | 21 wt % |
| 1,2,3-Trimethylbenzene | 1 wt % |
| 1,2,4-Trimethylbenzene | 5 wt % |
| 1,3,5-Trimethylbenzene | 13 wt % |

As a result, a product was obtained in an amount of about 420 Kg/hr. The product thus obtained was found to be a compound having the following general formula by Ms-, NMR-analysis and gas chromatography;

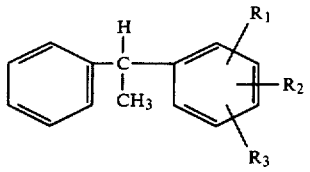

wherein $R_1$, $R_2$ and $R_3$ are hydrogen, methyl, ethyl, or isopropyl group, and the total carbon atom number of $R_1$, $R_2$ and $R_3$ was 3.

EXAMPLE [3] *8*

Purified tert-buthylbenzene obtained by refining a Light Alkane fraction from a detergent product plant was treated in the same way as in Example 1.

| | |
|---|---|
| tert-Buthylbenzene | 0.38 kl/hr |
| Styrene | 0.3 kl/hr |
| Recycle tert-buthylbenzene | 1.5 kl/hr |
| Sulfuric acid | 0.5 kl/hr |

As a result a product was obtained in an amount of about 400 Kg/hr. The compound thus produced had the following structural formula;

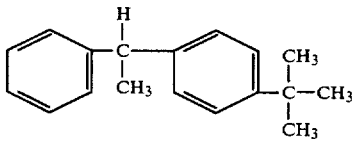

EXAMPLE 9

According to "Toxicology of Drugs and Chemicals", W. B. Deichmann and H. W. Gerarde; Academic Press in U.S.A., the acute toxicity of chlorinated biphenyl belongs in the group of "slightly toxic", from which it is considered to be relatively low toxic. However, when the chlorinated biphenyl is absorbed in the human body, there is no enzyme to metabolize it, and it can not be purged and is accumulated in the body. Accordingly, if it is absorbed by the body bit by bit for a long period of time, the accumulation of the chlorinated biphenyl causes impediments of the liver and the kidney. Therefore, the chronic toxicity by the use of chlorinated biphenyl has come into question.

The acute toxicity of the solvent of the present invention is 1.7 g/kg in $LD_{50}$ (rat, oral dose), which is about the same as those of common aromatic hydrocarbons and it is relatively low as the toxicity of one time dose.

Further, the subacute toxicity tests were carried out in order to appraise the chronic toxicity of the solvent of the present invention. In the subacute tests, each dose of the solvents of the present invention in the amount of one third ⅓ of said $LD_{50}$ value was given for one month, and any abnormal symptom could not be recognized in the body-weights, blood tests, serum diagnoses, urinalyses, weights of internal organs etc. Further, it was confirmed that the solvent of the invention was not accumulated in the body. Still further in the local stimulation tests on the skin and mucous membrane with regard to the product of the invention, any abnormal results such as rubefaction, acab, edema, congestion and puffiness were not recognized. Therefore, it will be understood from the above results that the product of the present invention is low toxic and is quite a safe material.

The chlorinated biphenyl which exists in the place not being exposed to the sun such as in a river, in the sea, in the soil and in a living body, is gradually accumulated on the earth if the production is still continued it will destroy nature, because it can not be decomposed by micro-organisms or metabolic enzymes. And recently, it has become a social problem as a source of the environmental pollution.

In the meantime, the product of the present invention has biodegradiability, accordingly it does not disturb the order of material cycles in nature.

The solvents of the present invention were tested according to the test method of biodegradability (SDA Procedure for the Determination of ABS/LAS Biodegradability, U.S.A.) which is used for the test of synthetic detergents. As the result of this test, it was understood that the solvents of the present invention were decomposed within a few days and the solvents could not be detected at all after one week.

According to said test standard, the biodegradability of detergent is specified as more than 85%/7 days, 8 days, while the values of the solvents of the present invention were 100%/7 days, 8 days. Accordingly, unlike the case of the chlorinated biphenyl, thhere is nothing to worry about the accumulation with regard to the solvent of the present invention.

EXAMPLE 10

Test of colour forming rate

A polymer which was prepared by condensing p-phenyl phenol and formaldehyde was dissolved as much as 5% into xylene, and a sheet of white paper was immersed into the obtained solution and dried. Then each 1% of C.V.L. (Crystal violet lactone) and B.L.M.B. (Benzeneleuco methyleneblue) was dissolved in the reaction product obtained from styrene and m-xylene in the foregoing Example, and thus obtained solution was dropped on said paper coated with phenol-polymer and was spread with using a pallette knife to form blue colour. The coloured paper was left for 24 hours at the room temperature and was used as the standard in the following test of the colour forming rate.

The solvent of the present invention was compared with partially nuclear hydrogenated terphenyl compound and monoisopropyl biphenyl which are practically used in place of the chlorinated biphenyl.

Each of the above solvents was added with each 1.5% by weight of C.L.V. and B.L.M.B. to obtain a solution of dyes. Then one drop of each solution was dropped on the phenol-polymer coated paper, and immediately thereafter, the drop was spread with a palette knife, and the colour formation was observed. Each time to give the colour which was equivalent to the previously prepared standard colour was measured, each result of which is shown in the following Table.

| | |
|---|---|
| Terphenyl compound partially nuclear hydrogenized | 118 seconds |
| Monoisopropyl biphenyl | 13 seconds |
| Solvent of the invention | 9 seconds |

From the above results, it will be understood that the solvent of the present invention is excellent.

EXAMPLE 11

1. Preparation of microcapsule

The solvents of the present invention as prepared by Examples 1 to 5 were used to form microcapsule by means of well known coacervation method.

C.V.L. (crystal violet lactone) was used as the dye-precursor. A mixed solvent consisting of 3 parts by weight of the above solvent and 1 part by weight of kerosene fraction ( Tradename; Nisseki No. 3 Ink Oil) as the auxiliary solvent was added with 3% of C.V.L., to obtain the dye solution.

The microcapsule prepared from the above dye solution was excellent as that prepared by using the chlorinated biphenyl. (2) Preparation of pressure sensitive record papers.

The microcapsule obtained in the above step (1) was used to coat on one side of a test paper (A), and clay was applied on one side of another test paper (B). While, the other paper (C) was coated with phenolaldehyde copolymer. Then, the coated surfaces of the papers (A) and (B) were put together, and the papers (A) and (C) were also put together. Each uncoated surface of the paper (A) was applied with a local pressure by hand writing. Thereby, blue copy lines were produced on the test papers (B) and (C), in which the copy lines were clear without run and the colour formation was satisfactorily quick.

What is claimed is:

1. A pressure sensitive record material which comprises a paper sheet coated with microcapsules holding internally a liquid containing a dye-precursor and at least one compound represented by the general formula:

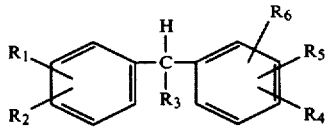

in which $R_1$ and $R_2$ are hydrogen; $R_3$ is methyl; $R_4$ and $R_5$ are hydrogen, methyl or ethyl; $R_6$ is an alkyl group selected from methyl, ethyl, n-propyl, isopropyl, sec-butyl and tert-butyl, and the total carbon atom number of $R_4$, $R_5$ and $R_6$ is 1–4.

*2. A pressure sensitive record material as claimed in claim 1 wherein the total carbon atom number of $R_4$, $R_5$, and $R_6$ is 3.*

*3. A pressure sensitive record material as claimed in claim 1 wherein said at least one compound is a mixture of compounds each having a total carbon atom number of $R_4$, $R_5$, and $R_6$ of 3.*

*4. A pressure sensitive record material as claimed in claim 2 wherein said at least one compound is a compound of the structural formula*

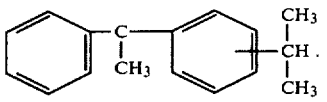

*5. A pressure sensitive record material as claimed in claim 1 wherein said at least one compound is a compound of the structural formula*

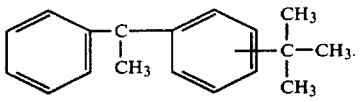

*6. A pressure sensitive record material as claimed in claim 1 wherein said at least one compound is a mixture of compounds each having a total carbon atom number of $R_4$, $R_5$, and $R_6$ of 1–2.*

*7. A pressure sensitive record material as claimed in claim 1 wherein said at least one compound is a mixture of compounds each having a total carbon atom number of $R_4$, $R_5$, and $R_6$ of 2.*

*8. A pressure sensitive record material as claimed in claim 7 wherein said at least one compound is a mixture of*

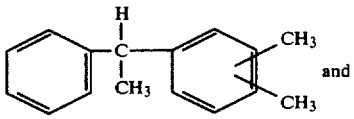

and

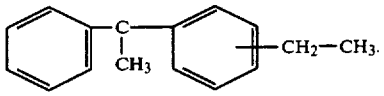

*9. A pressure sensitive record material as claimed in claim 1 wherein the total carbon atom number of $R_4$, $R_5$, and $R_6$ is 2.*

*10. A pressure sensitive record material as claimed in claim 9 wherein said at least one compound is*

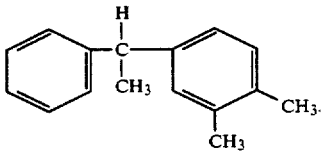

*11. A pressure sensitive record material as claimed in claim 9 wherein said at least one compound is a mixture of compounds of the structural formula*

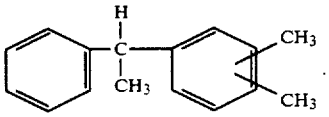

*12. A pressure sensitive record material as claimed in claim 9 wherein said at least at least one compound is*

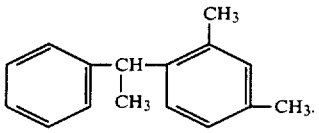

*13. A pressure sensitive record material as claimed in claim 9 wherein said at least one compound is a compound of the structural formula*

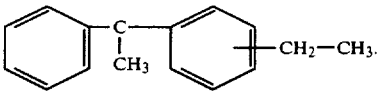

*14. A pressure sensitive record material as claimed in claim 9 wherein said at least one compound is a mixture of compounds of the structural formula*

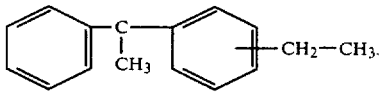

*15. A pressure sensitive record material as claimed in claim 1 wherein the total carbon atom number of $R_4$, $R_5$, and $R_6$ is 1.*

*16. A pressure sensitive record material as claimed in claim 15 wherein said at least one compound is a mixture of compounds of the structural formula*

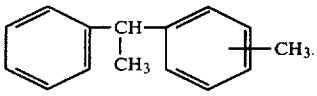

* * * * *